United States Patent [19]

Carrera et al.

[11] Patent Number: 5,227,294

[45] Date of Patent: Jul. 13, 1993

[54] **METHOD OF PRODUCING SURFACTIN WITH THE USE OF MUTANT OF *BACILLUS SUBTILIS***

[75] Inventors: Paolo Carrera; Paola Cosmina, both of Milan; Guido Grandi, Segrate, all of Italy

[73] Assignee: Eniricerche S.p.A., Milan, Italy

[21] Appl. No.: 718,464

[22] Filed: Jun. 20, 1991

[30] Foreign Application Priority Data

Jun. 22, 1990 [IT] Italy .................. 20738 A/90
Nov. 23, 1990 [IT] Italy .................. 22176 A/90

[51] Int. Cl.$^5$ .................. C12P 21/02; C12P 1/125
[52] U.S. Cl. .................. 435/71.2; 435/71.1; 435/252.31; 435/252.5
[58] Field of Search .................. 435/71.2, 71.1, 252.5, 435/252.31

[56] References Cited

U.S. PATENT DOCUMENTS

| | | | |
|---|---|---|---|
| 3,687,926 | 8/1972 | Arima et al. | 435/71.2 |
| 5,037,758 | 8/1991 | Mulligan et al. | 435/71.2 |
| 5,061,495 | 10/1991 | Rossall | 435/70.1 |

FOREIGN PATENT DOCUMENTS 1803987  6/1969  Fed. Rep. of Germany.

OTHER PUBLICATIONS

Chemical Abstacts, vol. 112, No. 15, Apr. 9, 1990 abstract No. 137408Q, Schmidt, M. et al: "Influence of Manganese Ions on Growth and Surfactin Formation of *Bacillus Subtilis*", p. 582 & Dechema Biotechnol, Conf. 1987 (publ. 1988), vol. 1; pp. 333-337.

Applied Microbiology and Biotechnology, vol. 31, No. 5/6, Oct. 1989, Springer Internatinal, pp. 486-489; Mulligan, C. et al.: "Enhanced Biosurfactant Production by a Mutant *Bacillus Subtilis* Strain".

*Primary Examiner*—Herbert J. Lilling
*Attorney, Agent, or Firm*—Sughrue, Mion, Zinn, Macpeak & Seas

[57] ABSTRACT

The present invention relates to a stable mutant of *Bacillus subtilis* which can produce surfactin with high yields, a method of producing surfactin with the use of the strain and the use of the surfactin obtained for pharmaceutical, energy and environmental problems.

11 Claims, 11 Drawing Sheets

METHOD OF PRODUCING SURFACTIN WITH THE USE OF MUTANT OF *BACILLUS SUBTILIS*

DESCRIPTION

The present invention relates to a stable mutant of *Bacillus subtilis* which can produce surfactin with high yields, a method of producing surfactin with the use of the strain, and the use of the surfactin produced for pharmaceutical, energy and environmental problems.

In recent years interest in biosurfactants of microbial origin for use as agents in the assisted recovery of hydrocarbons, the stabilisation of emulsions and, more generally, in the energy and environmental fields has increased considerably since these products are biodegradable and hence potentially less toxic than the synthetic compounds currently used.

A biosurfactant of particular interest, which is produced by *Bacillus subtilis*, is surfactin.

This compound, which was characterised by Kakinuma et al. [Agric. Biol. Chem., 33: 971-972 (1969); Agric. Biol. Chem., 33: 1523-1524 (1969); Agric. Biol. Chem., 33 973-976 (1969)], is a cyclic lipopeptide formed by a heptapeptide and a lipid portion constituted by a mixture of beta-hydroxy-fatty acids with chains having between 13 and 15 carbon atoms and has the following structure:

$$
\begin{array}{l}
\text{L—Leu—beta—OH—C}_{13-15}\text{—L—Glu—L—Leu} \\
\;\;\;| \hspace{5cm} | \\
\text{D—Leu—L—Asp}\text{————L—Val—D—Leu}
\end{array}
$$

Surfactin has the property of inhibiting the formation of blood clots and 3', 5' monophosphate diesterase and of lysing erythrocytes, spheroplasts and bacterial protoplasts.

Moreover, surfactin inhibits the fibrinogen-thrombin reaction, thus slowing the formation of fibrin; this property makes the substance suitable as an active element for the preparation of compositions useful as anticoagulants in the prophylaxis of thrombosis and for preventing diseases such as myocardial infarction, pulmonary embolism, etc., in general.

Surfactin shows anti-cholesterase activity, since it lowers the levels of cholesterol in the plasma and in the liver, as well as fungicidal and antibiotic activity.

The lipopeptide performs its bacteriostatic functions, for example, on the growth of mycobacteria, even at low concentrations (5-10 ppm).

Moreover, surfactin is a powerful surface-active agent and in fact reduces the surface tension of water from 72 mN/M to 27 mN/M at a concentration of 0.005%.

Its multiple activity means that surfactin is of particular interest, since it can be used widely in the pharmaceutical, energy and environmental fields.

Arima, K et al. (U.S. No. 3,687,926 and Biochem, Bioph. Res. Commun., 31: 488-494 (1968)) describe a method of perparing surfactin having the following structure:

$$
\begin{array}{l}
(\text{CH}_3)_2\text{CH(CH}_2)_9\text{CHCH}_2\text{CO—L—Glu—L—Leu—D—Leu—L—Val} \\
\;\;\;\;| \hspace{8cm} | \\
\;\;\;\;\text{——O————L—Leu—D—Leu—L—Asp}
\end{array}
$$

characterised by the use of the *B.subtilis* strain ATCC 21331 or ATCC 21332.

However, this method has disadvantages resulting from the low yields of surfactin (0.05-0.1 g/litre of the crude product and 0.04-0.05 g/l of the purified product).

Consequently, this method is not very acceptable economically from a commercial point of view.

Methods of improving surfactin yields have therefore been proposed in the art and these are based, essentially, on the use of particular culture media or mutants of the *B.subtilis* strain ATCC 21332 or particular technical solutions.

Thus, for example, Cooper D.G. et al., [(1981), Appl. Environ. Microbiol., 42: 408-412)]describe a method of producing surfactin by the culture of *B.subtilis* ATCC 21332 based, amongst other things, on the continuous removal of the foam which is produced during the fermentation and which contains 90-99% of the surfactin produced.

The object of removing the foam is to prevent the inhibiting effect which high concentrations of surfactin have on bacterial growth.

Under these conditions, however, a surfactin yield of 0.7-0.8 g/litre is achieved.

Moreover, the continuous removal of the foam may reduce the working volume of the fermentation medium which is discharged with the foam.

Sheppard J. and Mulligan C., (1987), (Appl. Microbiol. Biotechnol., 27: 110-116) describe a method by which a yield of 0.16 g/litre is obtained by the growth of *B.subtilis* cells in a medium supplemented with a hydrolysed peat protein.

Moreover, Mulligan, C. et al [Appl. Microbiol. Biotech., 31: 486-489 (1989)]describe a method for improving the yield of surfactin characterised by the use of a mutant of the *B.subtilis* wild-type strain ATCC 21332.

The authors report a surfactin yield of 0.562 g/litre after 40 hours (p. 488, Table 1), that is, about 3.4 times greater than that obtained by the growth of the wild-type strain under the same conditions.

In spite of the large amount of work carried out, therefore, no proposal has been found cheap enough to enable it to be developed on an industrial scale, mainly because of the low productivity of the micro-organisms available hitherto.

It has now been found that the problems of the prior art can be overcome by a new mutant of *B.subtilis* which can produce surfactin with high yields.

Samples of this mutant strain were deposited at the American Type Culture Collection on Apr. 23, 1990 and received the registration number ATCC 55033.

A subject of the present invention is therefore the *B.subtilis* strain ATCC 55033.

A further subject of the present invention is a method of producing surfactin with high yields including the use of the *B.subtilis* strain ATCC 55033.

Another subject of the present invention is the use of the surfactin produced in the pharmaceutical, energy and environmental fields.

Further subjects of the present invention will become clear from the following description and examples.

In particular, the *B.subtilis* strain ATCC 55033 according to the present invention is characterised by good genetic stability (the ability to retain the mutation acquired permanently) and good resistance to high concentrations of surfactin.

This strain was produced by the mutation of the *B.subtilis* wild-type strain ATCC 21332, which is commonly available to the public. For this purpose, it is possible to use conventional methods consisting of exposing cells of the wild-type strain to the action of chemical or physical mutagenic agents, selecting the strains in which the surfactin yield is altered and, finally, isolating those colonies in which productivity is increased.

Chemical mutagenic agents may be selected, for example, from diethyl sulphate, NMU (nitrosomethyl urethane), NMG (N-methyl-N'-nitro-N-nitrosoguanidine), and physical agents may be selected from X-rays, UV-rays (ultra-violet) and gamma rays in mutagenic doses.

According to one embodiment of the present invention, the *B.subtilis* wild-type strain ATCC 21332 was mutagenised with the use of NMG in concentrations such as to induce mutations in the genomes of the micro-organisms.

The mutants which could produce surfactin with high yields (the overproducer mutants) were then selected by analysing the sizes of the haemolysis haloes which appeared around the *B.subtilis* colonies grown on a culture medium such as, for example, TBAB (DIFCO) to which blood had been added.

In fact, it is known that the diameter of the haemolysis halo is proportional to the quantity of surfactin produced by the cells of *B.subtilis* (Mulligan, C. and Cooper, D. (1984), J. Ferment. Technol., 62: 158-179).

The overproductivity of the *B.subtilis* mutant ATCC 55033 thus isolated was then confirmed by the fermentation of the strain in question in a flask with the use of the wild-type strain as a control.

*B.subtilis* ATCC 55033 seems to be particularly suitable for producing surfactin with high yields by a fermentation method.

A method according to the invention may consist, for example, of preparing an inoculum of the mutagenised strain under aerobic conditions in an aqueous medium containing assimilable sources of carbon and nitrogen.

The medium is kept under agitation at a temperature between 25° and 40° C., preferably from 30° to 37° C. for a period shorter than 20 hours, preferably from 6 to 10 hours.

In fact, it has been found that an "old" inoculum (20 hours) causes foam production which is difficult to control to the point that after 5 hours the fermentation has to be stopped because of the extensive loss of the culture medium which is discharged with the foam.

"Young" inocula (6-10 hours) on the other hand enable the foam to form gradually with a limited loss of the culture medium.

A percentage of the inoculum of between 5% and 10% (volume/volume) of the working volume is then added to the fermentation medium which contains assimilable sources of carbon and nitrogen as well as various cations, anions and possibly vitamins such as biotin or thyamine and an aminoacid suitable for encouraging cell growth and the production of surfactin, selected from L-Valine, L-Leucine, D-Leucine and L-Isoleucine.

The initial cell density of the fermentation is generally equivalent to an $O.D._{600}$ of between 0.025 and 0.040.

Assimilable sources of carbon include carbohydrates such as glucose, hydrolysed starches, molasses, sucrose or other conventional carbon sources.

Examples of nitrogen sources may be selected, for example, from mineral ammonium salts such as ammonium nitrate, ammonium sulphate, ammonium chloride or ammonium carbonate, urea, or products containing organic or inorganic nitrogen such as peptone, yeast extract or meat extract.

The following cations and anions are also suitable for the purposes of the present invention: potassium, sodium, magnesium, iron, calcium, acid phosphates, sulphates, chlorides, manganese and nitrates.

According to the present invention a fermentation medium having the composition given in Example 2 is preferred.

The fermentation is carried out in a vessel (a fermenter or bioreactor) with stirring and intensive aeration, at a temperature usually between 25° and 40° C., preferably between 30° and 37° C., with the continuous removal of the foam formed which contains more than 98% of the surfactin produced.

Quantities of sterile compressed air which may vary from 0.2 to 1.0 vol/vol/minute are diffused into the fermentation medium.

The pH of the fermentation medium is kept between 6.0 and 7.2 and preferably between 6.7 and 6.9.

The pH may be adjusted, for example, by the addition of a basic aqueous solution such as an aqueous solution of ammonia, potassium hydroxide, sodium hydroxide, sodium carbonate or potassium carbonate.

It is preferable, however, to keep the pH to the desired value with the use of 10N sodium hydroxide (NaOH).

The stirring speed, which is one of the reasons for the production of the foam, is generally selected so as to allow high bacterial growth without having dramatic effects on the formation of the foam.

The initial stirring speed is typically between 150 and 400 rpm, preferably between 200 and 300 rpm.

Finally, the working volume of the fermentation which appears to be a critical element as regards the formation of the foam, is selected so as to limit the production of foam and hence the loss of the cellular biomass which is discharged with the foam produced.

The removal of the foam formed during the fermentation process reduces the working volume and results in the loss of the cells contained therein.

There are two possible approaches to overcome this problem. In one case, fresh sterile culture medium may be added to the bioreactor continuously (continuous fermentation) and, in the second case, the culture broth (containing the bacterial cells) which is discharged with the foam may be recycled into the bioreactor (the recycling of the culture medium).

According to a preferred embodiment of the method of the present invention, the culture medium which is eliminated with the foam removed is recycled to the bioreactor with the use, for example, of an automatic system as shown in FIG. 8.

Such a fermentation could present problems due to the fact that the concentration of the surfactin in the recycled medium could have an adverse effect on the further production of surfactin in the bioreactor because of the inhibiting effect of the substance on bacterial growth (Cooper et al.).

Surprisingly, however, the results obtained have shown an increase in the biomass and constant surfactin values in the bioreactor.

This indicates that the supply of a concentrated solution of surfactin from the collection container to the bioreactor has a limited effect on cell growth and that the surfactin has no inhibitory effect on its own synthesis by the mutant B.subtilis strain ATCC 55033.

These results suggest that, unlike the B.subtilis wild-type strain ATCC 21332, the mutant of the present invention may be more resistant to high concentrations of surfactin.

According to a further embodiment of the method of the present invention, the foam and the culture medium removed from the bioreactor may be treated by an ultrafiltration system assembled as shown in FIG. 12. The culture medium is then recycled to the bioreactor without the surfactin.

When the fermentation is carried out under the preferred conditions, a concentration of crude surfactin of from 2.0 to 4.0 g/litre is obtained within a period of from 40 to 90 hours.

At the end of the fermentation process, the surfactin is recovered from the foam and from the a cellular or cellular supernatant liquid and purified.

Conventional methods may be used for this purpose, such as, for example, precipitation by an inorganic acid such as sulphuric or hydrochloric acid or by a compound of a bivalent metal such as calcium, or by saturation with ammonium sulphate.

This treatment enables the selective precipitation of the surfactin and of some lipopeptides and lipoproteins produced by B.subtilis.

This precipitation step may be preceded by the treatment of the a cellular supernatant liquid by an ultrafiltration system in order to remove coarser impurities and concentrate the working volume to be purified.

The precipitate containing the surfactin is then purified with the use of one of the known techniques such as, for example, extraction with organic solvents such as chloroform or methylene chloride or saline precipitation by $CaCl_2$ or NaCl.

The method of the present invention produces quantities of from 1.2 to 2.0 g/litre of purified surfactin (99%).

The chemical-physical characterisation of the surfactin produced by the method of the present invention may be carried out by conventional methods with the use of chromatographic, spectroscopic or spectrometric techniques.

The results obtained by mass spectrometry (FAB), infrared spectrometry (IR), nuclear magnetic resonance (NMR) and high-pressure liquid chromatography (HPLC) confirmed the data in the literature.

Moreover, the presence of fatty-acid molecules which differ not only in the length of their carbon chains ($C_{13}$–$C_{15}$) but also in their structures which may be normal, iso or anteiso was confirmed.

The characterisation of the surface-active and aggregative properties of the surfactin produced by the method of the present invention confirmed the data in the literature.

The surfactin obtained by the method according to the present invention is therefore particularly suitable as a surface-active agent, as a stabilising agent for therapeutic compounds such as medication for the treatment of thromboses, embolisms and inflammation, and in the energy and environmental fields.

A photograph of a plate of TBAB (DIFCO) medium to which blood has been added, showing the haemolysis haloes of the B.subtilis wild-type strain ATCC 21332 and of the B.subtilis overproducer mutant ATCC 55033.

FIG. 2

A calibration curve in which the weight (g/l) of the solid biomass is shown on the ordinate and the absorbance at 600 nm is given on the abscissa.

FIG. 3

A curve correlating the diameter (cm) of the haemolysis halo produced on TBAB medium to which blood has been added (on the ordinate) with the quantity of surfactin (mg/ml) added to the medium (on the abscissa).

FIG. 4

A growth curve for the B.subtilis mutant ATCC 55033 showing time as a function of the absorbance measured at a wavelength of 600 nm and compared with the growth curve of the wild-type strain.

The time is expressed in hours on the abscissa and the absorbance ($0.D._{600}$) on the ordinate.

FIG. 5

A graph showing the cell growth and surfactin production detected during the fermentation of the B.subtilis mutant ATCC 55033 in a flask.

The time is shown in hours on the abscissa; the absorbance value of the cell culture at a wavelength of 600 nm is shown (on a logarithmic scale) on the ordinate on the left-hand side, and the quantity (g/l) of surfactin produced by B.subtilis ATCC 55033 is shown on the right-hand side.

FIG. 6

A graph showing the cell growth detected during the fermentation of the B.subtilis mutant ATCC 55033 in a flask in the presence of the aminoacids Val, Leu and Ile (*) and of Ile (o).

The time is shown in hours on the abscissa; the absorbance of the cell culture at a wavelength of 600 nm is shown (on a logarithmic scale) on the ordinate on the left-hand side.

FIG. 7

A graph showing the surfactin production during the fermentation of the B.subtilis mutant ATCC 55033 in a flask in the presence of the aminoacids Val +Leu +Ile (*) and Ile (o).

The time is shown in hours on the abscissa; the quantity (g/l) of surfactin produced is given on the ordinate on the right-hand side.

FIG. 8

A diagram showing a 2-litre fermenter with recycling in which:

1) is the fermenter, 2) is an air-inlet line, 3) is a pump, 4) is a used-air line, 5) is a foam-collection container and 6) is the line for recycling the culture medium.

FIG. 9

This drawing shows the rate of growth of the B.subtilis strain ATCC 55033 achieved in a 2-litre fermenter with the use of inocula of different ages.

The time is shown in hours on the abscissa; the growth rate is shown on the ordinate.

Figure 10:
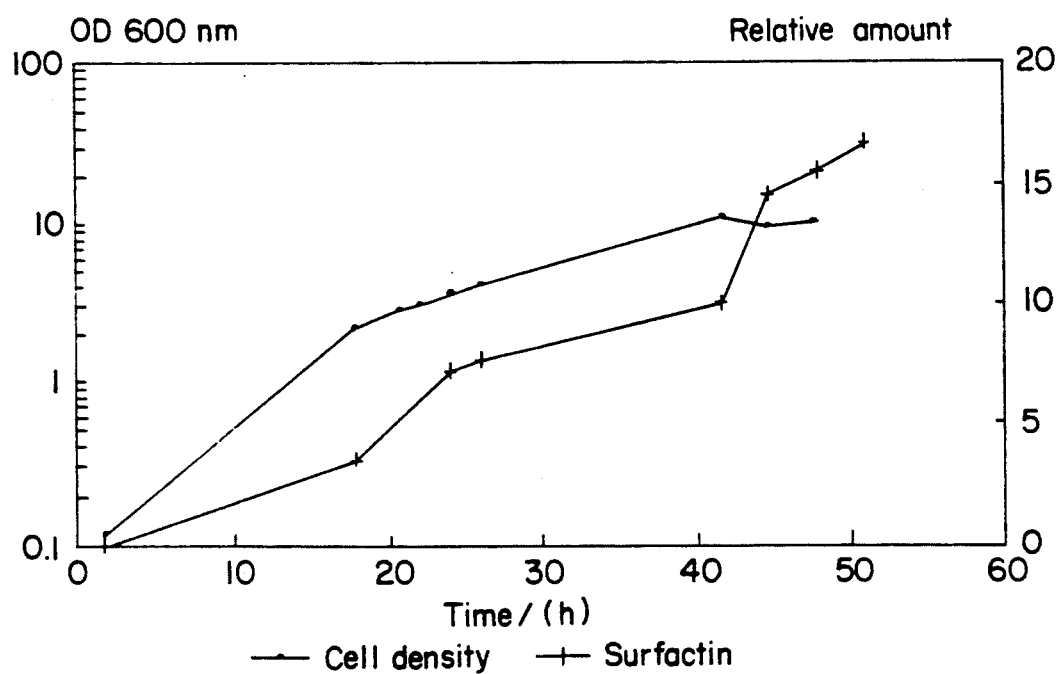
Figure 11:
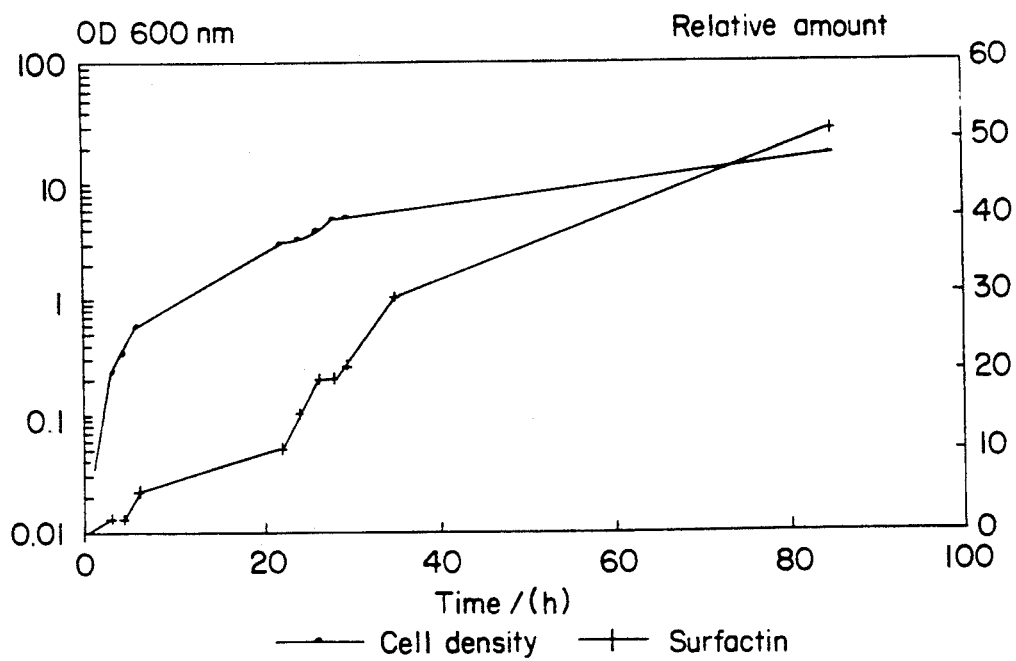

FIGS. 10 and 11

Graphs showing the cell growth and surfactin production detected during the fermentation of the B.subtilis mutant ATCC 55033 "with recycling".

The time is shown in hours on the abscissa; the absorbance value of the cell culture at a wavelength of 600 nm is shown (on a logarithmic scale) on the ordinate on the left-hand side, and the corresponding quantity detected by the measurement of the areas of the three main chromatographic peaks in which the presence of surfactin was shown is indicated on the right-hand side.

FIG. 12

A diagram showing the production of surfactin with the continuous ultrafiltration of the product, in which: 1) is the fermenter, 2) is an air-inlet line, 3) is a pump, 4) is a used-air line, 5) is a foam-collection container, 6) is an ultrafiltration cartridge and 7) is a container for the recycled culture medium.

FIG. 13

A) shows comparative curves of the growth of the B.subtilis mutant ATCC 55033 during fermentation with recycling and with ultrafiltration. The time is shown in hours on the abscissa; the absorbance value of the cell culture at a wavelength of 600 nm is given (on a logarithmic scale) on the ordinate.

B) compares the quantities of surfactin present in the bioreactor in a fermentation test with ultrafiltration and in a fermentation test with recycling.

The time is shown in hours on the abscissa; the quantity of surfactin (g/l) is given on the ordinate.

FIG. 14

A calibration curve correlating the quantity of surfactin expressed in g/l (abscissa) with the resulting value of the sum of the areas of six peaks produced by HPLC analysis (ordinate).

FIG. 15

A chromatographic profile of a 25 μg sample of purified surfactin. The three main peaks are constituted by surfactin bound to fatty acids with lengths varying between 13 and 15 carbon atoms.

FIG. 16

The chromatographic profiles of this drawing are the result of the direct analysis of 50 μl of the acellular supernatant liquid withdrawn during fermentation. The profiles relate to samples taken 3, 4, 27 and 30 hours after the start of the experiment. The presence of the product is shown clearly by the appearance and subsequent development of the chromatographic peaks relating to the various components of surfactin (C13-C14-C15)

FIG. 17

The characterisation of a sample of purified surfactin by the FAB (Fast Atom Bombardment) technique. The main peaks shown relate to products having molecular weights of 1008, 1022 and 1036 respectively, and corresponding to surfactin fractions bound to beta-fatty acids with chains of various lengths.

FIG. 18

An IR (infrared ray) spectrum of a sample of purified surfactin. The interpretation of the spectrum is given in Example 6C.

The present invention will be described further by the following examples.

EXAMPLE 1

Preparation of the B.subtilis mutant which is an overproducer of surfactin

A preculture of the B.subtilis wild-type strain ATCC 21332 (available from the American Type Culture Collection) was grown at 37° C. for one night on Schaeffer sporulation medium having the following composition:

| | |
|---|---|
| Nutrient broth (DIFCO) | 8.0 g/l |
| KCl | 1.0 g/l |
| MgSO$_4$ | $1.25 \times 10^{-1}$ g/l |
| Agar (DIFCO) | 16.0 g/l |
| MnCl$_2$.4H$_2$O | $1.98 \times 10^{-3}$ g/l |
| FeSO$_4$.7H$_2$O | $2.78 \times 10^{-4}$ g/l |
| Na$_2$SO$_4$ | $1.42 \times 10^{-1}$ g/l |
| H$_2$O | 1 liter |
| pH | 7.0 |

A loop of the preculture was then used to inoculate 10 ml of DIFCO VY medium (Veal Infusion Broth 25 g/l and yeast extract 5 g/l) and grown at 37° C. for 16 hours.

A portion (100 μl) of the culture was transferred into a 100 ml flask containing 10 ml of fresh VY medium and grown with gentle stirring (200 revolutions per minute, rpm) at 37° C. until an optical density (O.D.) of 0.7 determined at 600 nm by a Beckman spectrophotometer (mod. DU70) was achieved.

The bacterial cells were then separated from the supernatant liquid by centrifuging at 5,000 rpm for 10 minutes with the use of a Mod. SS. 34 rotor on a Sorvall supercentrifuge, washed with 5 ml of TM buffer (Tris-HCl 0.05M, maleic acid 0.05M, (NH$_4$)$_2$SO$_4$ 1 g/litre, MgSO$_4$.7H$_2$O, 0.1 g/litre, Ca(NO$_3$)$_2$ 5 mg/litre, FeSO$_4$.7H$_2$O0.25 mg/litre) brought to pH 6.0 with 5N NaOH, separated again by centrifuging in the manner described above, and resuspended in 5 ml of TM buffer.

5 ml of a solution of hydrated N-methyl-N'-nitro-N-nitrosoguanidine (1:1 with H$_2$O) (Fluka) in TM buffer (0.3 mg/ml) was then added to the cellular suspension and then incubated with stirring at 37° C.

After 30 minutes the suspension was centrifuged again and the cells recovered were washed with 5 ml of TM buffer and then resuspended in 50 ml of fresh VY medium.

Portions (1 ml) of the suspension were grown with gentle stirring at 37° C. for one night and, after the addition of 0.2 ml of sterile glycerol, were frozen at −80° C.

The B.subtilis mutants were then selected by the spreading of serial dilutions (about $2 \times 10^2$ cells/plate) of the portions on TBAB medium plates (Tryptose Blood Agar Base (DIFCO) 33 g/litre) to which 5% of defibrinated ram's blood (SCLAVO S.p.A.,) filtered through sterile gauze had been added, after sterilisation at 120° C. for 20 minutes.

Figure 1:
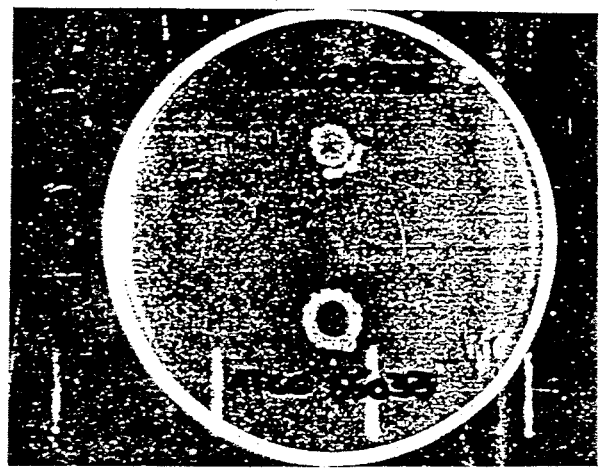
FIG. 1

After thermostatically-controlled incubation at 37° C. for 16–24 hours, the diameter of the haemolysis haloes which appeared around the bacterial colonies were determined (FIG. 1).

In fact, it is known that the size of the haemolysis halo is proportional to the quantity of surfactin produced by the B.subtilis cells (Mulligan, C. and Cooper, D. (1984), J. Ferment. Technol., 62: 158 –179).

One of the surfactin-overproducer colonies, designated B.subtilis SMS 274, was deposited as ATCC 55033.

EXAMPLE 2

Production of surfactin in a flask

A colony of B.subtilis SMS 274 was used to inoculate 10 ml of VY medium and grown at 200 rpm, at 37° C. for 16 hours.

100 μl of this preculture were then transferred into a flask with a capacity of 2 litres containing 1 litre of minimum medium having the following composition:

| | |
|---|---|
| Glucose | 40.00 g/l |
| NH$_4$Cl | 4.00 g/l |
| KH$_2$PO$_4$ | 4.00 g/l |
| NaHPO$_4$ | 5.64 g/l |
| MgSO$_4$.7H$_2$O | 0.20 g/l |
| CaCl$_2$.2H$_2$O | 1.00 × 10$^{-3}$ g/l |
| FeSO$_4$.7H$_2$O | 20.00 × 10$^{-3}$ g/l |
| MnCl$_2$.4H$_2$O | 1.98 × 10$^{-4}$ g/l |
| EDTA | 1.50 × 10$^{-3}$ g/l |
| pH | 7.0 |

The culture was carried out with stirring (250 rpm) at 37° C. for 24 and 48 hours in a New Brunswick thermostatically-controlled incubator.

In all the experiments the B.subtilis strain ATCC 21332 grown under the same conditions was used as a control.

Figure 2:
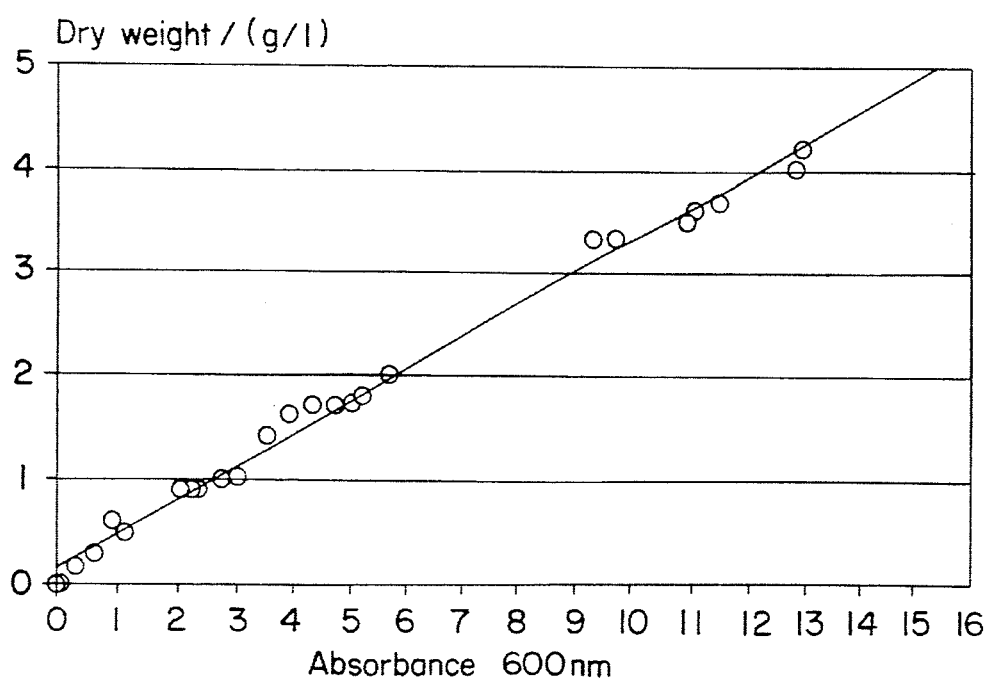

Cell growth (biomass) was monitored by the determination of the optical density of the culture broth at 600 nm (DU 70 spectrophotometer, Beckman Instruments, Inc., USA) with the use of dishes with optical paths of 1 cm (Bio-Rad Laboratores, USA). The O.D. values were then converted to g/l by means of a standard curve produced with the use of various dilutions (of known weights) of the solid biomass of the micro-organism (FIG. 2).

The surfactin was determined by the deposition of portions of the a cellular supernatant liquid produced after the centrifuging of 2 ml of culture broth (Biofuge A, Heraeus Sepatech, FRG) at 7,000 rpm for 5 minutes at 4° C. on TBAB medium plates to which blood had been added and the determination of the sizes of the haloes formed The supernatant liquid was diluted by 1:10,000 with distilled water.

The degrees of haemolysis of the blood cells (the sizes of the haloes) were used as indications of the surfactin productivities of the micro-organisms.

Figure 3:
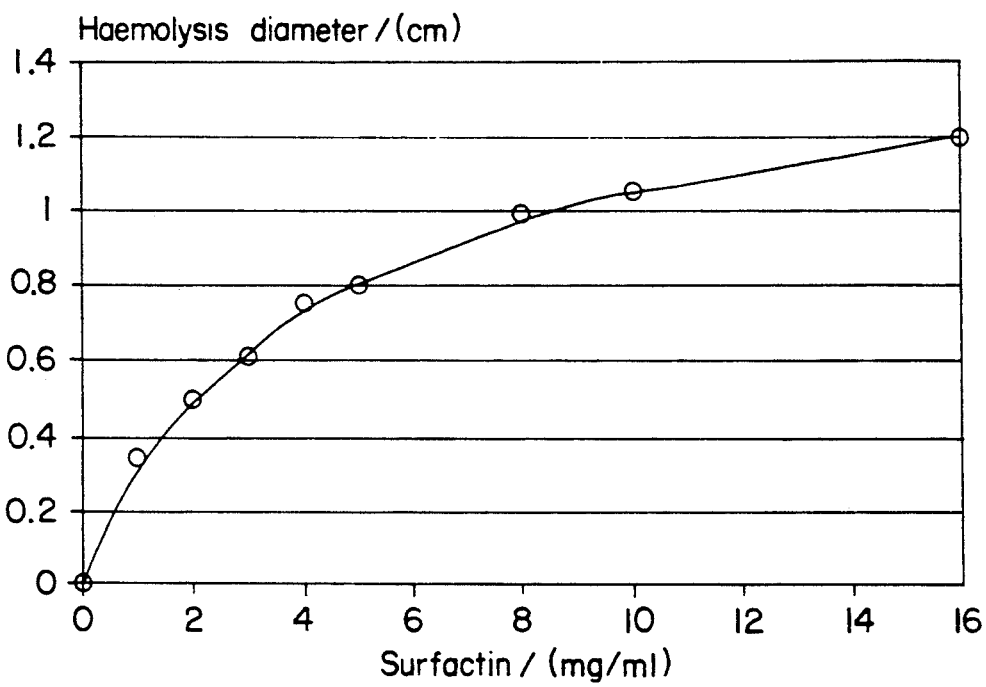

Estimates of the yields were made by means of a standard curve correlating the sizes of the haemolysis haloes with known concentrations of surfactin (FIG. 3).

Figure 4:
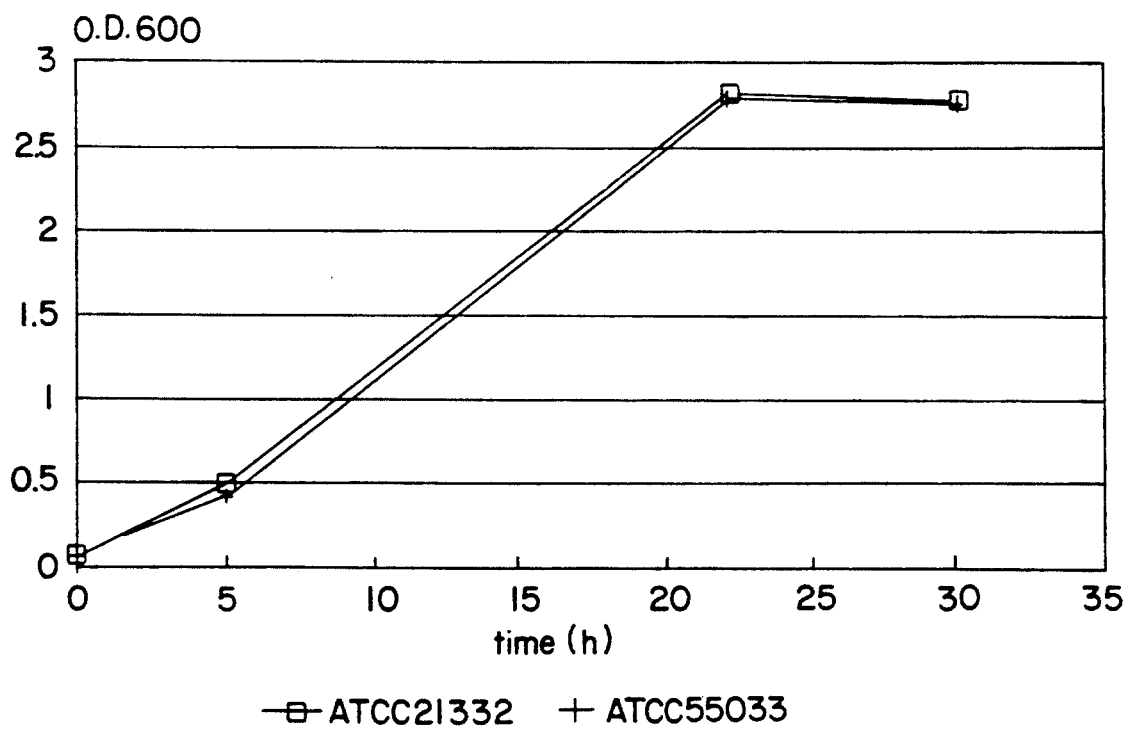

FIG. 4 shows the growth curves of the mutant SMS 274 and of the wild-type strain ATCC 21332 obtained by the determination of the O.D.$_{600}$ values over a period of time.

It can be seen from an analysis of this drawing that the growth of the B.subtilis mutant SMS 274 is wholly comparable to that of the wild-type strain.

Figure 5:
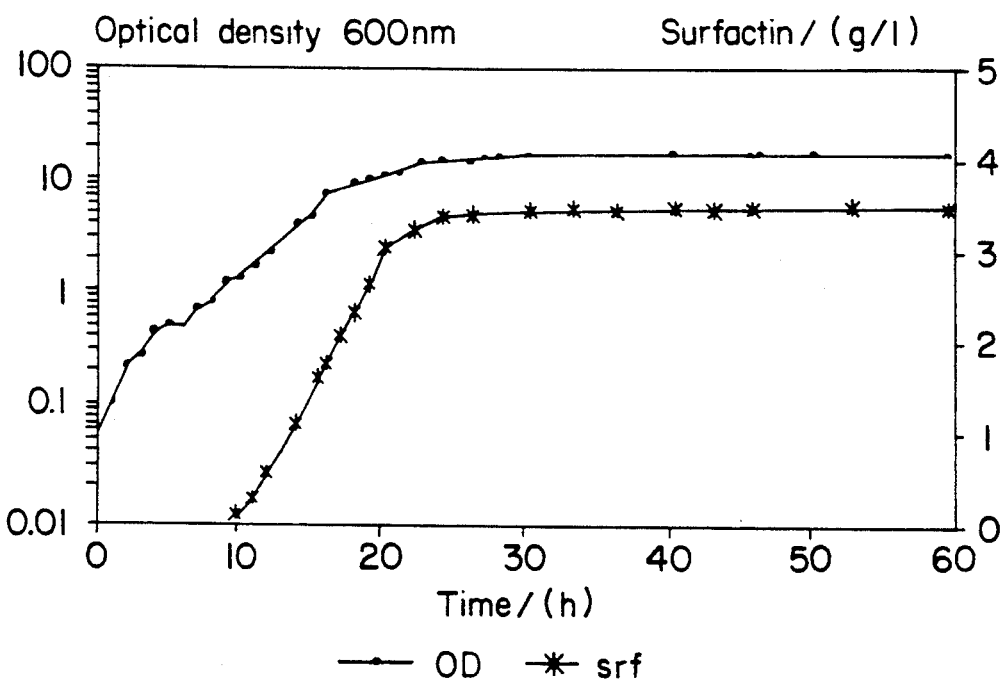

FIG. 5 shows the surfactin growth and production curves for the mutant SMS 274 and for the wild-type strain.

It can be seen from this drawing that determinable levels of surfactin are present 10 hours after the start of the fermentation, that is, at the start of the truly logarithmic stage. The amount of surfactin present in the fermentation medium increases linearly, in comparison with the stationary growth phase, at an accumulation rate (ΔP/Δt) of about 0.32 g/1h. A surfactin value of 3.5 g/l is reached during the stationary phase. In this test only the quantity of surfactin present in the culture medium, which is approximately comparable to the total surfactin yield, was determined.

EXAMPLE 3

Investigation of the effect of aminoacids on the growth and production of surfactin by B.subtilis SMS 274

A series of tests was carried out to check the effects of aminoacids on the growth and production of surfactin by the mutant SMS 274.

The tests were carried out as in Example 2 in 2-litre flasks each containing 1 litre of minimum medium supplemented with 5 mg/l of each of the following aminoacids: L-Leucine (Leu), L-Valine (Val), L-Isoleucine (Ile) and D-Leucine.

Figure 6:
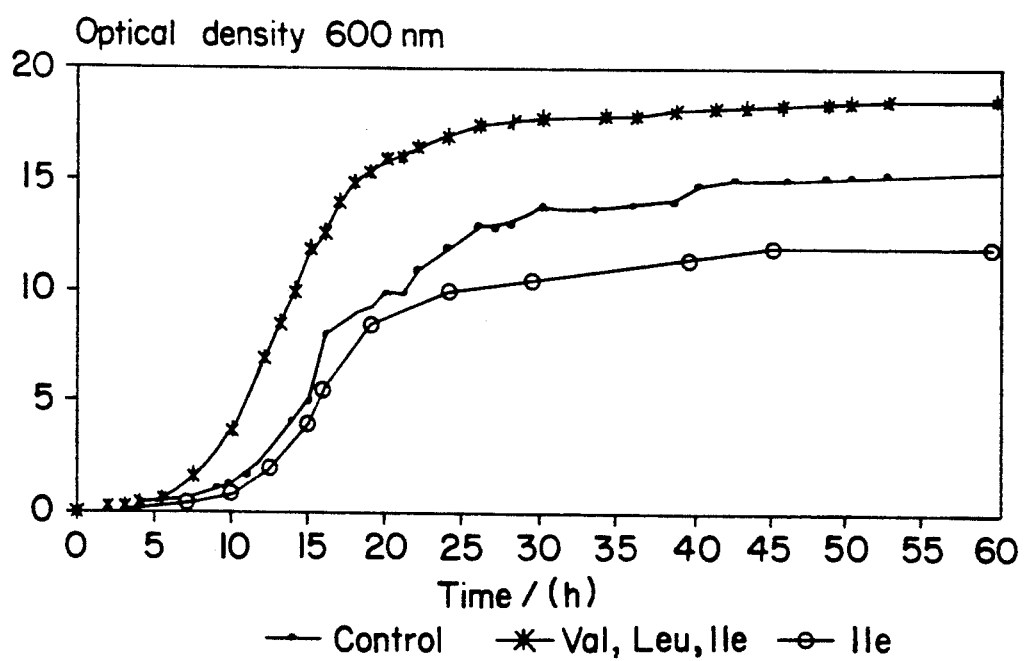

The results showed that the presence of the three aminoacids L-Leu, L-Val and L-Ile in the fermentation medium induced an increase in the biomass (FIG. 6).

Figure 7:
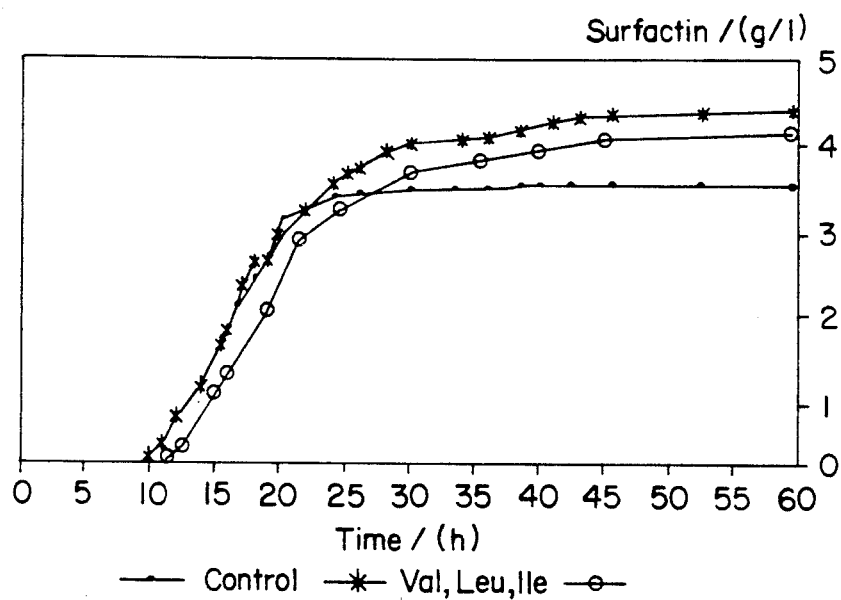

During the first 20 hours, the surfactin production was similar to that obtained in the control (the same strain grown in a medium without additional aminoacids), however, the surfactin content in the medium increased during the stationary phase and at the end of the fermentation the quantity of surfactin was about 30% greater than that found in the control (FIG. 7) and Table 1.

When only Ile was added to the fermentation medium, it was observed that cell growth was inhibited and there was a delay of 1 hour in the formation of surfactin. 60 hours after the start of the fermentation, however, there was an increase of about 20% in the surfactin produced in comparison with the control and the surfactin to cell ratio was 1.19, indicating an increase in the cellular production of surfactin.

TABLE 1

| Aminoacids | srf$_{60}$ g/l (+/−10%) | OD$_{60}$ 600 nm (+/−5%) | srf$_{60}$/biomass g/l per g/l (+/−10%) |
|---|---|---|---|
| Val + Ile + Leu | 4.5 | 18.8 | 0.75 |
| Ile | 4.2 | 11.0 | 1.19 |
| D-Leu | 3.6 | 16.0 | 0.74 |
| control | 3.5 | 15.0 | 0.74 |

Note: the surfactin srf was determined by HPLC analysis after 60 hours.

EXAMPLE 4

Production of surfactin in a fermenter with recycling

The object of the test was to check the effects on the surfactin yield of parameters such as the age of the inoculum, the stirring and the working volume.

A slant preculture of the strain B.subtilis SMS 274 was used to inoculate a 100 ml flask containing 10 ml of VY medium and incubated with gentle stirring at 37° C. for 16 hours.

500 ml flasks each containing 100 ml of minimum medium were then each inoculated with 1 ml of the preinoculum and some were kept at 37° C. with stirring at 350 rpm for 6 hours ("young" inocula) and others for 20 hours ("old" inocula).

The cultures (100 ml) were then used to inoculate a fermenter with a capacity of 2 litres controlled by an electronic control unit (Instrumentation Laboratories) for monitoring and automatically correcting the temperature, the pH, the dissolved oxygen and the stirring speed.

The inocula were added to 1 litre of minimum medium sterilised directly in the fermenter, producing final working volumes of from 1.1 to 1.6 litres.

The initial optical density of the culture (at the time $t_0$), determined at 600 nm with the use of a Beckman spectrophotometer (mod. DU 70) was 0.035 on average.

The initial fermentation conditions were:

| | |
|---|---|
| temperature | 37° C. |
| aeration | 0.6–0.7 vol/vol/minute |
| stirring | 200–700 rpm |
| pH | 6.8–6.9 |

These parameters were kept constant automatically throughout the fermentation period and, in particular, the pH was kept at about 6.8 by the addition of 10N NaOH.

The fermentation period was between 10 and 90 hours.

During the fermentation, the initial stirring speed of 200–220 was brought to about 400 rpm to keep the $p_{O2} > 15\%$.

Figure 8:
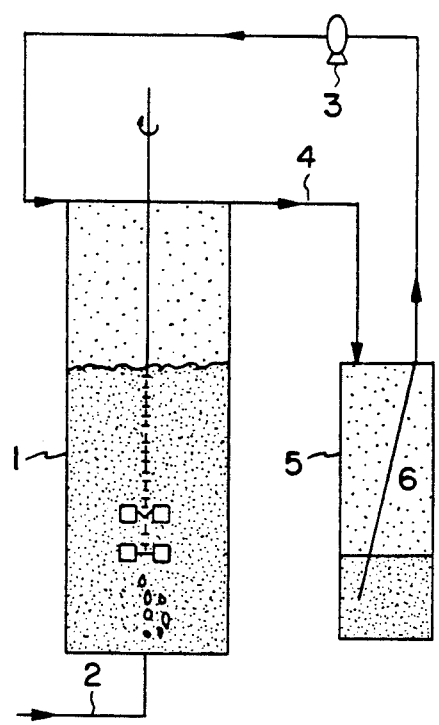

The foam produced during the fermentation was removed continuously with the use of an exhaust-air outlet line of the fermenter (FIG. 8).

About 20 hours after the start of the fermentation, that is, when an appreciable amount of surfactin and hence of foam had been produced, a system for recycling the culture medium discharged from the bioreactor with the foam was activated by means of a pump in order to keep the working volume constant.

During the fermentation, the cell growth was monitored by the determination of the optical density at 600 nm and the surfactin in the a cellular supernatant liquid was determined by HPLC analysis as described in Example 8.

Figure 9:
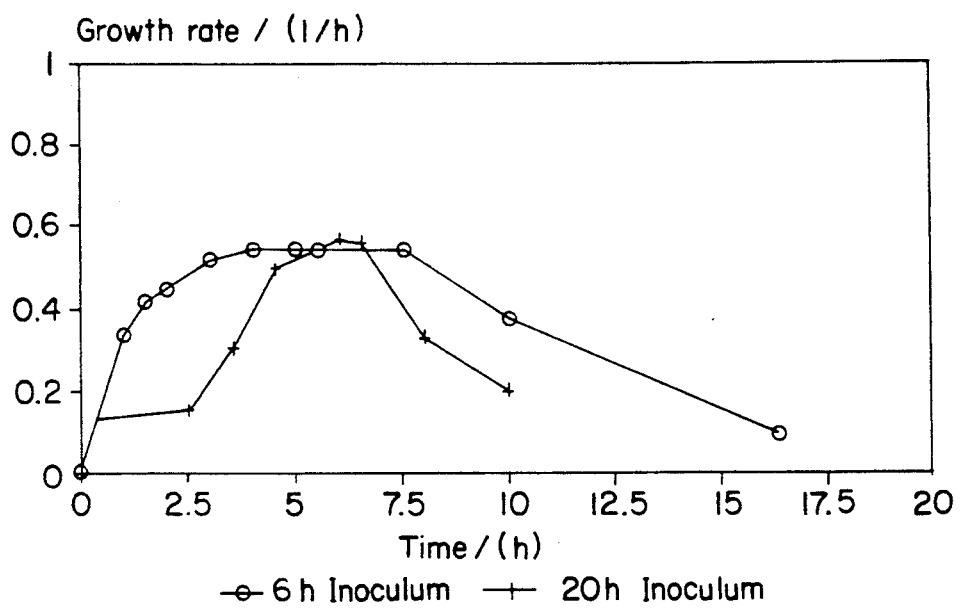

The data obtained showed that:

the best results were obtained with initial stirring at from 200–220 rpm; in fact faster stirring (500–700) caused foam production which was difficult to control to the extent that 5 hours after the start of the fermentation the experiment had to be stopped because of the excessive loss of the culture broth.

unlike a "young" inoculum (6 hours), an "old" inoculum (20 hours) caused rapid and uncontrolled foam production only 5 hours after the start of the fermentation (FIG. 9).

a working volume $\leq 1.6$ litres (from 1.1 to 1.41) is preferable.

Under the preferred conditions, cell growths equivalent to 12 and 15 units of absorbance (O.D. 600), corresponding to about 4 g/1 of solid bacterial biomass (for a final O.D.$_{600}$ of 15) were observed after 47 hours (FIG. 10) and 80 hours (FIG. 11), respectively. The surfactin was purified from the acellular supernatant liquid and from the foam resulting from the fermentation by the method described in point b) of Example 7.

The results in terms of the yield of the purified product obtained after 47 and 80 hours were 1.20 g/l and 2.0 g/l, respectively.

EXAMPLE 5

Fermentation with the continuous ultrafiltration of the surfactin

Figure 12:
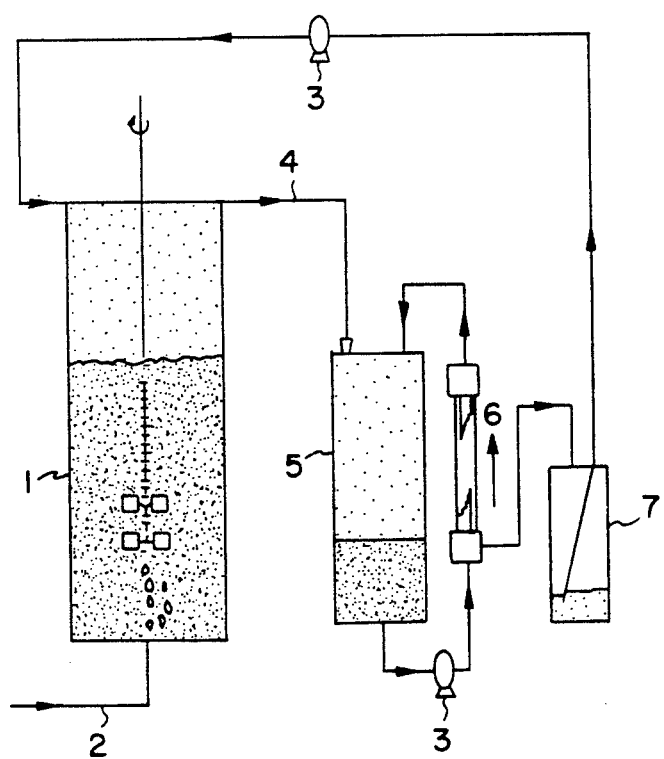

The system included an on-line ultrafiltration system connected to the fermenter (FIG. 12).

The system proposed provided for the continuous removal of the surfactin produced during the fermentation by the treatment of the foam and some of the fermentation broth (that which was discharged as a result of the pressure created in the fermenter) in ultrafiltration equipment (Amicon mod. CH2A) constituted by a collection container, a peristaltic pump and a hollow-fibre ultrafiltration cartridge (Amicon mod. H1P30-43) with a nominal cut-off of 30,000 daltons.

As shown in FIG. 12, the liquid from the fermenter passed through the cartridge (6) and most of the surfactin (more than 95%) was retained in the ultrafiltration system in the form of aggregates. A pump system (3) returned the culture medium to the fermenter without the product in question.

During the fermentation, cell growth was monitored (by the determination of the optical density at 600 nm) and the production of surfactin was monitored (by the chromatographic technique described in Example 8, point A). Table 2 shows comparative data from a fermentation test with ultrafiltration and from a fermentation test with a recycling system assembled as in Example 4.

TABLE 2

| | Surfactin | |
|---|---|---|
| Sections | Ultrafiltration | Recycling |
| Fermenter | 0.046 g | 3.157 g |
| Foam | — | 0.706 g |
| Filtered liquid | 0.082 g | — |
| Retained liquid | 3.002 g | — |
| | 3.002 g | 3.863 g |
| Final optical density O.D.$_{600}$ | 7.2 units | 15.5 units |
| Surfactin/biomass | 1.36* | 0.78* | where:
* = grams of surfactin per gram of biomass per liter calculated according to the following formula:

$$\frac{\text{g of surfactin}}{\text{units (O.D.}_{600}) \times 0.318 \text{ (correction factor)}}$$

65 hours after the start of the fermentation, the cell growth was equivalent to 7.2 absorbance units (O.D.$_{600}$) corresponding to about 2.3 g/liter by weight of solid bacterial biomass.

system was then purified from the acellular medium by the method described in point b) of Example 7.

The result in terms of the yield of purified surfactin was 1.88 g/litre.

Figure 13A:
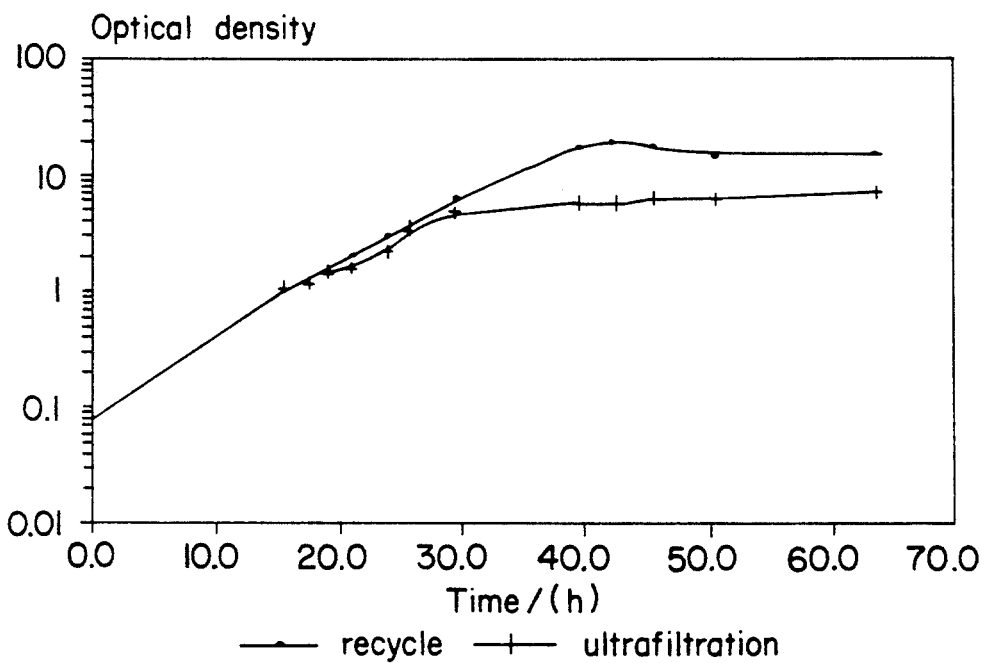
Figure 13B:
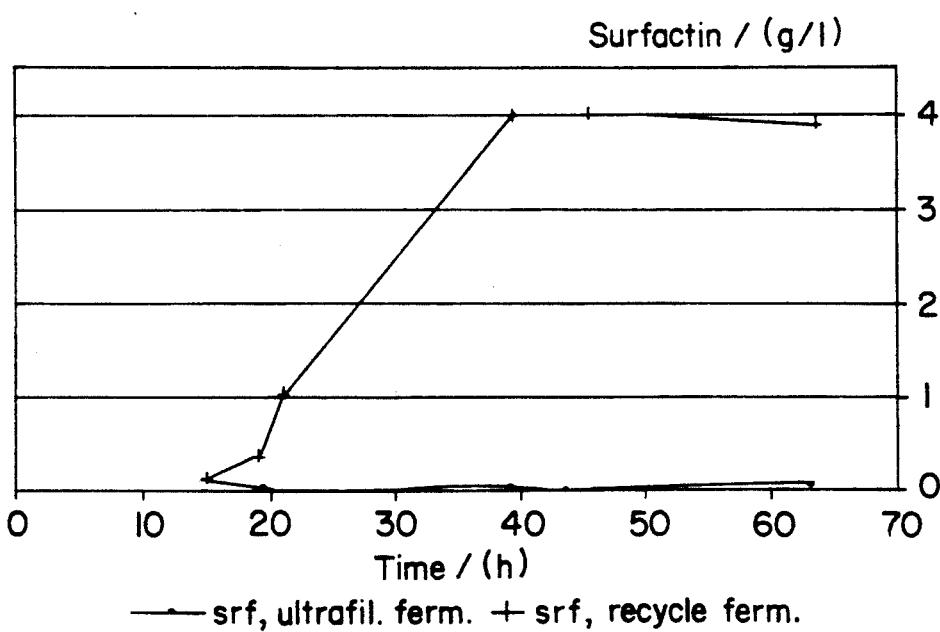

FIG. 13 shows the data for cell growth (A) and the efficiency of the removal of the surfactin (B) compared with those achieved by fermentation with recycling alone.

EXAMPLE 6

Production of surfactin in a 20-litre fermenter with recycling

A SETRIC G.A. fermenter mod. SET.20 with a capacity of 20 litres was used and contained 11 litres of minimum medium having the composition given in Example 2.

A 6-hour preculture (1 litre) of *B.subtilis* SMS 274 produced as described in Example 4, was transferred into the fermenter (a 10% inoculum). The final working volume was thus 12 litres.

In this experiment a system for continuously removing the foam produced and recycling the fermentation medium was also used.

The fermentation was carried out at 37° C. with aeration at 0.5 vol/vol/minute, initial stirring at 200–220 rpm and a pH of about 6.8, kept at that value by 10N NaOH solution.

The other parameters were kept constant automatically throughout the duration of the experiment.

17–18 hours after the start of the fermentation, the foam generated in the surface layer in the reactor was collected in the collection container together with some of the fermentation medium and, after 28 hours, the pump for recycling the fermentation medium was activated to re-establish the working volume in the bioreactor.

During the stationary phase, the cell growth reached an $O.D._{600}$ of 6.6 with an increase 5–6 times that obtained in a 2-litre fermenter.

At the end of the fermentation 21 g (1.8–1.9 g/1) of purified surfactin were obtained.

EXAMPLE 7

Isolation and purification of the surfactin

After the bacterial cells had been removed by centrifuging at 5,000 rpm for 10 minutes in a Sorvall centrifuge with the use of a mod. GS.3 rotor, the surfactin may be recovered from the accellular supernatant liquid and from the foam from the fermentation process by two alternative methods:

a) Concentration by ultrafiltration followed by extraction as in point (b)

This treatment has the objects of (1) reducing the volume to be treated in the subsequent purification step (b) and (2) removing from the supernatant liquid compounds with low molecular weights which might be precipitated together with the surfactin during the subsequent purification step (b).

Portions of the acellular supernatant liquid were treated in Amicon mod. 8101 ultrafiltration equipment. The system consisted of a cartridge (Amicon) with a cut-off of 30,000 daltons containing 55 hollow ultrafiltration fibres, a peristaltic pump and a reserve container for the sample.

The liquid retained by the fibres returned to the reserve container of the ultrafiltration system whilst the liquid (containing substances with low molecular weights) was removed from the system. The surfactin was recovered from the reserve container.

Upon HPLC analysis, it was observed that more than 95% of the surfactin produced was present in the retained liquid.

b) Acidification and extraction with organic solvents

The acellular supernatant liquid and the foam from the fermentation process, or the liquid from step a) were brought to pH 2.0 by the addition of 6N HCl.

The resulting flocculate was separated from the solution by centrifuging at 10,000 rpm for 15 minutes in a Sorval centrifuge (rotor Mod. GS-3) and dried under vacuum with the use of a Rotavapor 461 (Büchi, Switzerland).

The crude product thus isolated was resuspended in organic solvents such as chloroform or dichloromethane and, after stirring for one night, the resulting mixture was filtered through Whatmann No. 4 filter paper to remove the coarser impurities.

The filtrate thus obtained was then extracted twice with equal volumes of distilled $H_2O$ with a pH between 7.0 and 9.0 with gentle stirring for about 15 minutes. After this period, the mixture was placed in a separating funnel and left for several hours to allow the two phases to separate. The aqueous phases containing the surfactin were withdrawn, combined and acidified to pH 2.0 by the addition of 6N HCl. The surfactin, which was precipitated in the form of whitish granules, was recovered by centrifuging at 10,000 rpm, dried under vacuum and possibly weighed to evaluate the yield.

EXAMPLE 8

Characterisation of the purified surfactin

A) HPLC Chromatographic analysis

Samples of purified surfactin were dissolved in an elution buffer [50% n-propanol in 0.1% TFA (trifluoracetic acid)] to give a final concentration of between 0.1 and 1.0 mg/ml and then analysed by HPLC.

A Beckman chromatographic system was used and was constituted by two pumps Mod. 110 B, a controller Mod. 421 A, a UV detector Mod. 163 and a Shimadzu integrator mod. C-R3A.

A Licrospher ® 100 RP-18 column (5 μm) with a Licrospher ® 100 RP-18 precolumn (5 μm) (Merck) was used for the chromatographic separations.

The chromatographic conditions were:

| | |
|---|---|
| temperature | ambient (20–25° C.) |
| flow rate | 0.5 ml/minute |
| UV detector | 220 nm |
| eluent | 50% n-propanol in 0.1% TFA |
| volume injected | 100 μl |
| separation time | 30–40 minutes. |

The HPLC analysis was used to characterise the purity and quantity of the chromatographic sample and also to follow the production of surfactin over a period of time during the fermentation.

Figure 14:
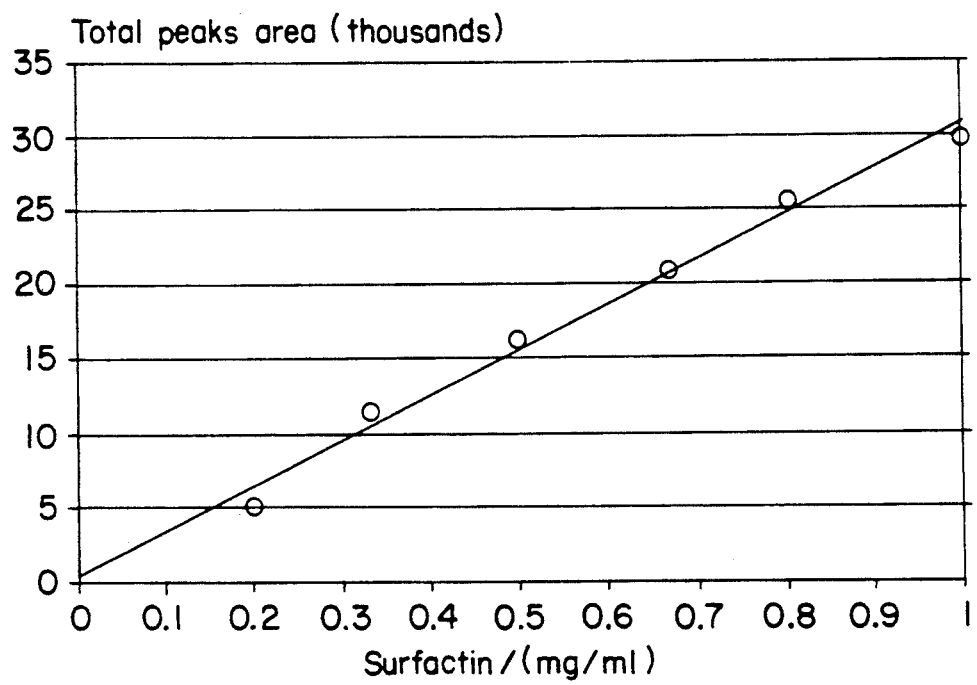

The standard curve shown in FIG. 14, in which the sum of the areas of six peaks is plotted as a function of the concentration of the surfactin, was used for this purpose.

An equal volume of n-propanol +0.1% TFA was added to samples of the acellular supernatant liquid (50μl) possibly diluted with distilled water, and then injected into the column.

Figure 15:
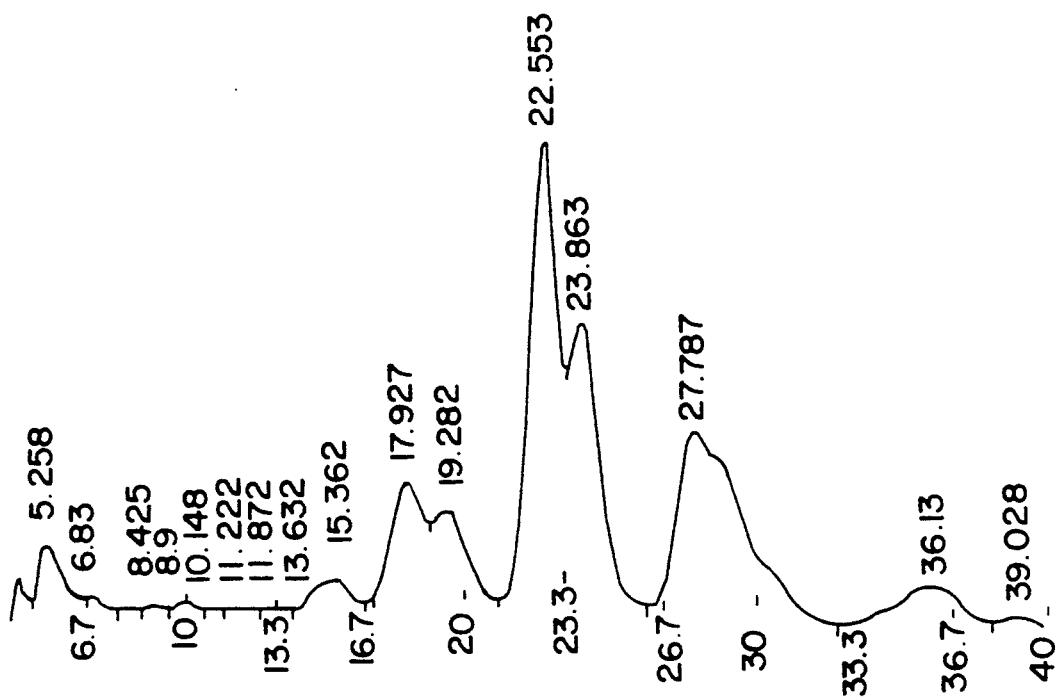
Figure 16A:
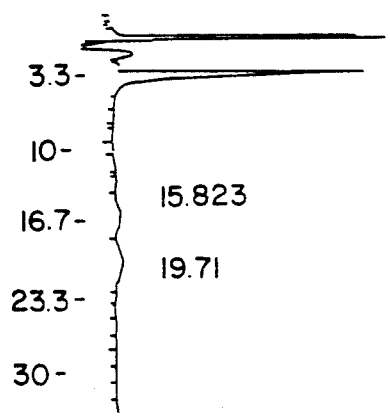
Figure 16B:
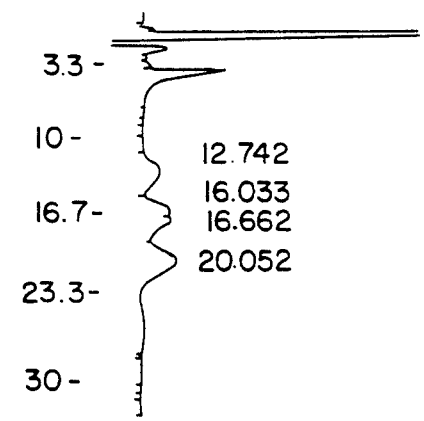
Figure 16C:
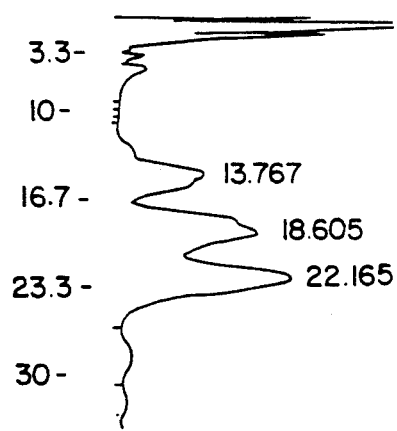
Figure 16D:
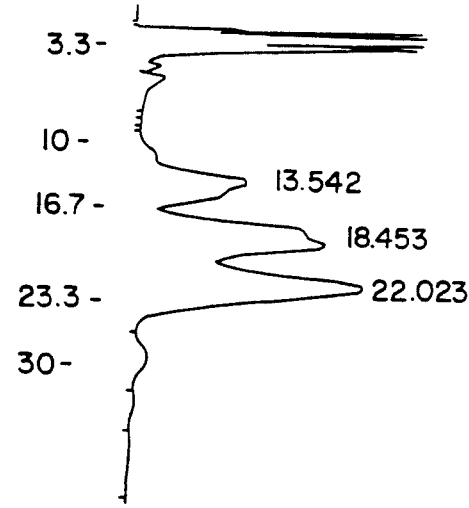

FIG. 15 shows the separation of a 50 μg sample of purified surfactin, and FIG. 16 shows the surfactin produced during fermentation with recycling after the strain had been grown for 3, 4, 27 and 30 hours.

B) Mass spectroscopy

The molecular weights of the compounds under test were determined by mass spectrometry.

A Finnigan mass spectrometer mod. MAT/90 equipped with an Iontech Atom gun supplied with Xenon gas accelerated at 7KV by FAB ionisation (Fast Atom Bombardment) was used for the analysis.

Either glycerol-thioglycerol (1:1, v/v) or p-nitrobenzyl alcohol was used as the matrix.

The mass spectra were recorded by a data integration system and calibration was effected automatically with the use of a perfluorokerosine mixture (PFK).

The analysis was carried out both on purified surfactin samples and on individual fractions produced by preparatory chromatographic separation (HPLC) carried out as described in point A).

Figure 17:
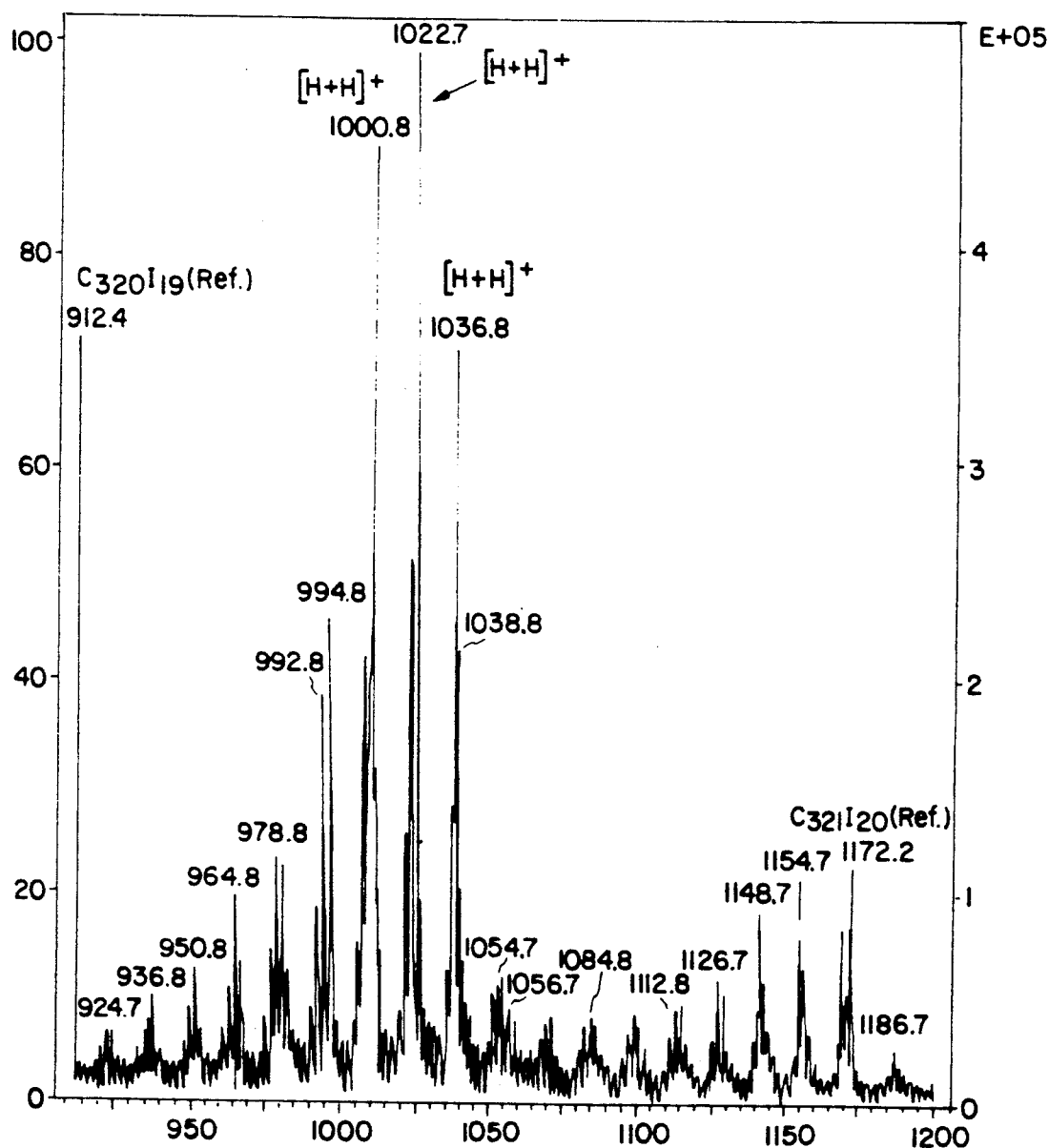

The spectra for the former samples indicated the presence of three main peaks with masses [M+H]+ of 1008, 1022 and 1036 respectively (FIG. 17).

These results conform to those given by C.N. Mulligan et al. [Appl. Microbiol. Biotechnol., 31: 486–489, (1989)].

Mass spectra obtained for the individual fractions showed the presence of at least 6 different components the nature of which can be explained by the presence of fatty-acid molecules with normal, iso and anteiso structures.

C) Infrared analysis (IR)

In order to confirm the exact structure of the surfactin obtained with the use of the mutated *B.subtilis* SMS 274 strain, a purified sample was subjected to infrared analysis by the following method:

after the sample had been dispersed in KBr (1 mg of surfactin in 300 mg of KBr), the resulting suspension was ground in an agate dish in a vibration mill for about 5 minutes, homogenised and then placed in a tablet press. The sample was subjected to a pressure of 10 tonnes/cm$^2$ to produce a transparent pellet which was dried at 60° C. under vacuum for one night.

The sample thus treated was then analysed by a spectrometer with a Digilab interferometer mod. FTS15E.

Figure 18:
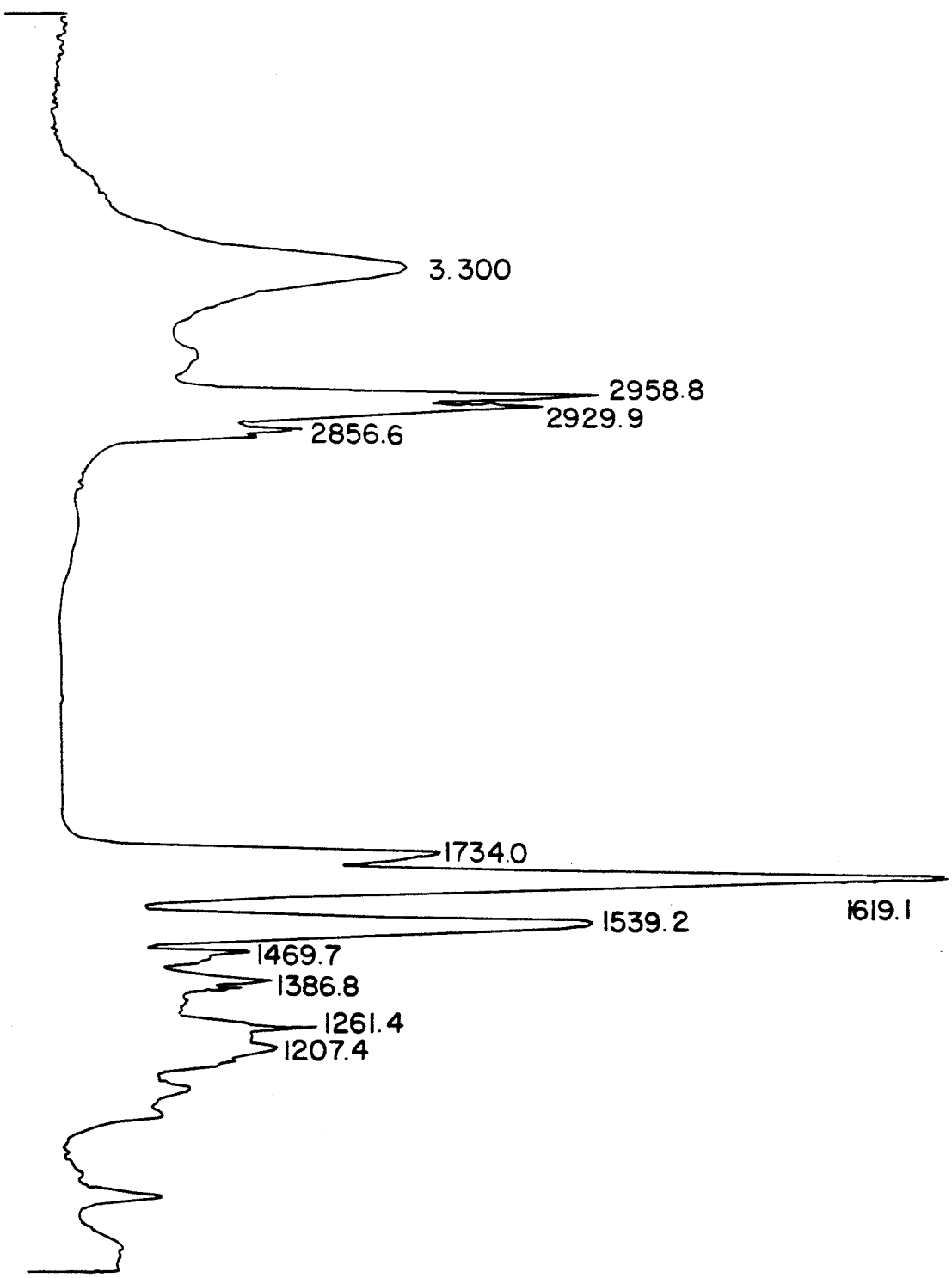

The data of the spectrum (FIG. 18) may be interpreted thus:

1. C-H region

The absorption bands at 2958, 2929 and 2856 cm$^{-1}$ are predominant and indicate the —CH$_3$ group. The data also show the presence of a large number of —CH$_2$ groups. The band at 1470 cm$^{-1}$ is a vibration deformation of the —CH$^2$ and —CH$^3$ groups.

2. C=O region

The strong band at 1649 cm$^{-1}$ is due to secondary amides. The second strong band at 1539 cm$^{-1}$ corresponds to the —CO—NH—R group. A third semi-weak amide band is observed at 1261 cm$^{-1}$, whilst a strong band observed at 1734 cm$^{-1}$ is due to a carbonyl group.

3. CH$_2$, CH$_3$ bending deltaCH$_2$ delta CH$_3$ between 1470 and 1380 cm$^{-1}$ 1470 = deltaCH$_2$ + deltaCH$_3$ 1380 delta$_{sym}$CH$_3$ is stronger and indicates a preponderance of CH$_3$, the presence of geminal CH$_3$s and, probably, the effect of a C=O at beta.

4. (O—H) and (N—H) Absorption

The spectrum shows vibrations of the O—H and N—H bonds at 3070 and 3300 cm$^{-1}$. These correspond to the following groups:

3070 cm$^{-1}$: —CO—NH
3300 cm$^{-1}$: =N—H

The results obtained conformed to those published by H. Kratzschmar et al [J. of Bacteriol., 170: 5347-5353, (1988)].

We claim:

1. A method for producing surfactin comprising the steps of:
   (a) growing, in a fermentation vessel, *Bacillus subtilis* strain ATCC 55033 under aerobic conditions in a liquid culture medium containing assimilable sources of carbon, nitrogen, and inorganic salts, and optionally containing vitamins and amino acids, at a pH o between 6.0 and 7.2 and a temperature of between 25° and 42° C. wherein the amount of surfactin produced is at least 2.0 g/liter of crude surfactin in 40 hours,
   (b) removing foam formed from the fermentation vessel, and
   (c) separating and purifying surfactin from the culture medium.

2. The method according t claim 1, wherein the culture medium present in the foam removed in step (b) is recycled to step (a).

3. The method according to claim 1, wherein the surfactin present in the culture medium and in he foam is removed by an ultrafiltration system and the culture medium, less the surfactin, is recycled to step (a).

4. The method according to claim 1, wherein the assimilable source of carbon is selected from the group consisting of carbohydrates, hydrolysed starches and molasses.

5. The method according to claim 4, wherein said carbohydrate is selected from the group consisting of glucose and sucrose.

6. The method according to claim 5, wherein said carbohydrate is glucose.

7. The method according to claim 1, wherein the assimilable source of nitrogen is selected form eh group consisting of mineral ammonium slats, urea and substances containing organic or inorganic nitrogen.

8. The method according to claims 7, wherein said mineral ammonium slats are selected from the group consisting of ammonium nitrate, ammonium sulfate, ammonium chloride and ammonium carbonate.

9. The method according to claim 7, wherein said substances containing organic or inorganic nitrogen are selected from the group consisting of peptone, yeast extract and meat extract.

10. The method according to claim 1, wherein said amino acids are selected from the group consisting of L-leucine, D-leucine, L-valine and L-isoleucine.

11. The method according to claim 1, wherein there is obtained at least 1.2 g/litre of purified surfactin in step (c).

* * * * *